(12) United States Patent
Harakawa et al.

(10) Patent No.: US 9,278,133 B2
(45) Date of Patent: Mar. 8, 2016

(54) **HIGHLY PURIFIED TYPE A *BOTULINUM* TOXIN PREPARATION FROM INFANT BOTULISM PATHOGEN**

(75) Inventors: Tetsuhiro Harakawa, Kumamoto (JP);
Hirotoshi Nakano, Kumamoto (JP);
Yasushi Torii, Kumamoto (JP);
Yoshitaka Goto, Kumamoto (JP); Miho Shinmura, Kumamoto (JP); Sachio Okuda, Kumamoto (JP); Ryuji Kaji, Naruto (JP); Shunji Kosaki, Tondabayashi (JP)

(73) Assignees: THE CHEMO-SERO-THERAPEUTIC RESEARCH INSTITUTE, Kumamoto (JP); TOKUSHIMA UNIVERSITY, Tokushima (JP)

( * ) Notice: Subject to any disclaimer, the term of this patent is extended or adjusted under 35 U.S.C. 154(b) by 87 days.

(21) Appl. No.: 12/447,351

(22) PCT Filed: Oct. 26, 2007

(86) PCT No.: PCT/JP2007/070927
§ 371 (c)(1),
(2), (4) Date: Apr. 27, 2009

(87) PCT Pub. No.: WO2008/050866
PCT Pub. Date: May 2, 2008

(65) Prior Publication Data
US 2010/0173841 A1 Jul. 8, 2010

(30) Foreign Application Priority Data

Oct. 27, 2006 (JP) ................................ 2006-293173

(51) Int. Cl.
*A61K 38/48* (2006.01)
*A61K 39/08* (2006.01)
*A61K 9/00* (2006.01)
*A61K 47/42* (2006.01)
*A61K 9/19* (2006.01)

(52) U.S. Cl.
CPC .............. *A61K 47/42* (2013.01); *A61K 9/0019* (2013.01); *A61K 38/4893* (2013.01); *A61K 9/19* (2013.01)

(58) Field of Classification Search
None
See application file for complete search history.

(56) References Cited

U.S. PATENT DOCUMENTS

| 5,756,468 | A | 5/1998 | Johnson et al. | |
|---|---|---|---|---|
| 8,273,359 | B2 * | 9/2012 | Favre et al. ................ | 424/239.1 |
| 2005/0084504 | A1 | 4/2005 | Aoki et al. | |
| 2010/0187689 | A1 * | 7/2010 | Kulkarni et al. ............ | 257/738 |
| 2011/0033431 | A1 * | 2/2011 | Nakahira et al. ........... | 424/93.41 |
| 2013/0252902 | A1 * | 9/2013 | Nakahira et al. ............ | 514/18.3 |
| 2014/0154781 | A1 * | 6/2014 | Favre et al. ................. | 435/220 |

FOREIGN PATENT DOCUMENTS

| EP | 1273593 A1 | 1/2003 |
|---|---|---|
| EP | 1491205 A1 | 12/2004 |
| EP | 1640017 A1 | 3/2006 |
| WO | 9611699 A1 | 4/1996 |
| WO | 0113357 A1 | 2/2001 |

OTHER PUBLICATIONS

Arimitsu et al (Infection and Immunity, Mar. 2003, vol. 71, No. 3, p. 1599-1603).*
Kozaki et al (Microbiol. Immunol. 39(10), 1995, p. 767-774).*
Simpson et al, Neurology® 2008;70:1691-1698.*
Koguma, et al.,"Soyakuto Human Science Research Institute Priority Study Report," 2003, pp. 97-100.
Yokoyama et al.,"Translational research using purified botulinum neurotoxin type A," The Nishinihon journal of urology, 2006, pp. 234-238.
Sakaguchi et al.,"Distinct characters of Clostridium botulinum type A strains and their toxin associated with infant botulism in Japan," International journal food microbiology, 1990, pp. 231-242, vol. 11.
Jankovic et al.,"Botulinum toxin in movement disorders," Current opinion neurology, 1994, pp. 358-366.
Kaji et al.,"Dystonia and botulinum therapy," Shindan-To-Chiryosha, 2005.
Kubota et al.,"Gene arrangement in the upstream region of Clostridium botulinum type E and Clostridium butyricum BL6340 progenitor toxin genes is different from that of other types," FEMS Microbiolgy letter, 1998, pp. 215-221.
Kubota et al., Mosaic type of the nontoxic-nonhemaggulutinin component gene in Clostridium botulinum type A strain isolated from infant botulism in Japan, Biochemical and Biophysical research communications, 1996, pp. 843-848.
Kozaki et al.,Immunological characterization of the neurotoxin produced by Clostridium botulinum type A associetd with infant botulism in Japan, Microbiol. Immunol., 1995, pp. 767-774.
Cordoba et al., Studies on the genes encoding botulinum neurotoxin type A of Clostridium botulinum from a variety of sources, System. Appl. Microbiol., 1995, pp. 13-22, vol. 18, Gustav Fischer Verlag, Jena, New York.
Arimitsu et al.,Purification of fully activated clostridium botulinum serotype B toxin for treatment of patients with dystonia, Infection and Immunityc, 2003, pp. 1599-1603, vol. 71, No. 3.

(Continued)

*Primary Examiner* — Nita M Minnifield
(74) *Attorney, Agent, or Firm* — Browdy and Neimark, PLLC

(57) ABSTRACT

A novel type A *botulinum* toxin preparation is provided. A neuromuscular transmission blocking agent comprising as an active ingredient a highly purified type A *botulinum* toxin from *Clostridium botulinum* as infant botulism pathogen and a medicament for treating a disease with a muscle overactivity comprising as an active ingredient said toxin. In particular, the medicament of the present invention, as compared to the conventional known *botulinum* toxin preparations, has rapid efficacy of potential and is less diffusive and thus, having a broader safety margin, may be used as therapeutic medicament for decreasing local, muscle overactivity in a disease with a muscle overactivity.

11 Claims, 5 Drawing Sheets

(56) References Cited

OTHER PUBLICATIONS

Tse et al.,"Preparation and characteristics of homogeneous neurotoxin type A from clostridium botulinum: Its inhibitory action on neuronal release of acetylcholine in the absence and presence of beta-bungarotoxin," Eur. J. Biochem., 1982, pp. 493-500, vol. 122-, No. 3.

Supplementary European Search Report issued in corresponding European Patent Application No. EP07830661 mailed Dec. 15, 2011.

Smith et al., Sequence variation within botulinum neurotoxin serotypes impacts antibody binding and neutralization, Infection and Immunity, 73(9):5450-5457 (2005).

Willems et al., Sequence of the gene coding for the neurotoxin of Clostridium botulinum type A associated with infant botulism: comparison with other clostridial neurotoxins, Research in Microbiology, 144(7):547-556 (1993).

Torii et al., Comparison of effects of botulinum toxin subtype A1 and A2 using twitch tension assay and rat grip strength test, Toxicon, 57(1):93-99 (2011).

Pier et al., Botulinum neurotoxin subtype A2 enters neuronal cells faster than subtype A1, FEBS Letters, 585 (1):199-206 (2010).

Dodd et al., A comparison of the spread of three formulations of botulinum neurotoxin A as determined by effects on muscle function, European Journal of Neurology, 5(2):181-186 (1998).

Communication of Inquires issued in corresponding Japanese Patent Application No. 2008-541036 dated Feb. 12, 2014, and English translation thereof.

Keiji Koguma et al., IBotulinus Dokuso Seizai no Rinsho Ohyo, Igaku-no-ayumi, "Clinical application of botulinum neurotoxin preparation," 216(3):251-252 (2006).

Genji Sakaguchi et al., International Journal of Food Microbiology, Elsevier, "Distinct characters of Clostridium botulinum type A strains and their toxin associated with infant botulism in Japan", 11:231-242 (1990).

Guangyun Lin et al., Applied and Environmental Microbiology, "Expression of the Clostridium botulinum A2 Neurotoxin Gene Cluster Proteins and Characterization of the A2 Complex", 76:(1)40-47 (Jan. 2010).

Sakaguchi et al., "Purification and Oral Toxicities of Clostridium Botulinum Progenitor Toxins" Biomedical Aspects of Botulism, Academic Press New York, pp. 21-34 (1981).

* cited by examiner

Fig. 1

| | Structure | M.W.(kDa) |
|---|---|---|
| LL Toxin | NTX NTNH HA / NTX NTNH HA | 900 |
| L Toxin | NTX NTNH HA | 500 |
| M Toxin | NTX NTNH | 300 |
| S Toxin | NTX | 150 |

Fig. 2 a : Stimulating electrode (+)
b : Stimulating electrode (−)
c : Recording electrode (−) and administration site
d : Recording electrode (+)
e : Ground electrode
f : Electrode for recording diffusion (−)
g : Electrode for recording diffusion (+)

Time after administration (hour)

| Toxin tested | CMAP-ED$_{50}$ | CMAP-SD$_{50}$ | Therapeutic window |
|---|---|---|---|
| NTX | 0.138 | 4.864 | 35.25 |
| 62A NTX | 0.117 | 2.695 | 23.03 |
| BOTOX | 0.188 | 3.350 | 17.82 |

HIGHLY PURIFIED TYPE A *BOTULINUM* TOXIN PREPARATION FROM INFANT BOTULISM PATHOGEN

TECHNICAL FIELD

The present invention relates to a neuromuscular transmission blocking agent comprising as an active ingredient a type A neurotoxin of 150 kDa obtained from HA-negative, type A *Clostridium botulinum* isolated as infant botulism pathogen, and a medicament for treating a disease with a muscle overactivity comprising said neurotoxin as an active ingredient.

BACKGROUND ART

A *botulinum* toxin produced by *Clostridium botulinum*, anaerobic Gram-positive bacteria, is the most lethal neurotoxin on earth. It is classified into seven types, A, B, C, D, E, F and G, and the property of each type has been elucidated. The types are distinguishable from each other by respective type-specific neutralizing antibodies. Depending on the types, a *botulinum* toxin may vary in animal species it may affect, severity of paralysis it induces, duration of time of its action, and the like. An active center protein of a *botulinum* toxin has a molecular weight of about 150 kDa (NTX) as common in all the known seven types.

Any *botulinum* toxin, when produced from *Clostridium botulinum*, is a complex composed of NTX and relevant non-toxic proteins. A type A *botulinum* toxin is produced in a molecular form of either 900 kDa (LL toxin), 500 kDa (L toxin), or 300 kDa (M toxin) (FIG. 1). These *botulinum* toxins are separate to release NTX and NTNH (a nontoxic protein) under alkaline conditions (pH 7.2 or higher). By utilizing this property, it is possible to isolate NTX of 150 kDa (an active center protein that endows a neurotoxin with the activity; also called "S toxin") alone. These LL, L and M toxins are called a *botulinum* toxin complex or a progenitor toxin. These *botulinum* toxins are, upon absorption in the upper small intestine, separate to release nontoxic proteins and a neurotoxin in a lymphatic vessel. The released neurotoxin is then bound to a receptor at the nerve end at its C-terminus of a heavy chain and taken into neurons via the receptor. Then, it specifically cleaves a protein in the presynaptic membrane through a light chain zinc methaloendopeptidase activity and inhibits a calcium-dependant release of acetylcholine to thereby block neuromuscular transmission at the synapse (Non-patent reference 1).

Although a *botulinum* toxin is a neurotoxin that may lead human to death in *botulinum* intoxication through blockage of systemic neuromuscular transmission, it may also be utilized as a remedy for treating a disease with a muscle overactivity such as e.g. dystonia by positively making use of its activity and by administering directly into the muscle of a patient suffering from the disease so that a local muscular tension may be relieved (Non-patent reference 2). For instance, a type A *botulinum* toxin complex (Allergan Inc., BOTOX; registered trademark) has been approved as a medicament for treating blepharospasm, strabismus, hemifacial spasm, and cervical dystonia, and for treating wrinkles at the middle of the forehead by the Food and Drug Administration (FDA). A seritype B *botulinum* toxin complex (Elan Pharmaceuticals, MYOBLOC; registered trademark) has also been approved as a medicament for treating cervical dystonia by FDA. It is said that a type A *botulinum* toxin has a higher potency and a longer duration of action as compared to types other than a type A *botulinum* toxin. An average duration of action of a type A *botulinum* toxin from its single muscular administration up till amelioration of symptoms is typically about 3 to 4 months.

In recent years, the action of *botulinum* toxin has been proved at (1) the neuromuscular conjunctions, (2) the ganglions of the autonomic nerves, (3) the terminal of the postganglionic parasympathetic nerve, (4) the terminal of the postganglionic sympathetic nerve, and (5) the pain receptive fibers. For the neuromuscular conjunctions of the skeletal muscles, the terminal of the muscarinic acetylcholinergic nerves is the main active site. Among the ganglions of the autonomic nerves, it is conceived that a direct action to the ganglions of the parasympathetic nerves is related to a clinic action. It is also reported that the action to the peripheral autonomic nerves causes inhibition of release of ATP, VIP (vasoactive intestinal polypeptide) or substance P or inhibition of the action of NO (nitric oxide) synthetase. It also became known that *botulinum* toxin is useful for alleviating pain. In this action, it is reported that *botulinum* toxin inhibits release of glutamic acid, substance P and CGRP (calcitonin gene-related peptide) (Non-patent reference 2). As such, *botulinum* toxin is a useful neuromuscular transmission blocking agent that inhibits release of various neurotransmitters at various nerves.

Currently, a biological potential of a therapeutic preparation of a *botulinum* toxin such as a type A *botulinum* toxin is indicated as a mouse $LD_{50}$ unit. One $LD_{50}$ is defined as $LD_{50}$ which is, based on intraperitoneal administration to mice, defined as an amount with which a half number of mice tested dies. Namely, a potential is quantified with a level or an amount of a neurotoxin with which mice die as a consequence of respiratory muscular relaxation. One $LD_{50}$, i.e. one unit, in mice of commercially available type A *botulinum* toxin complex (Allergan, Inc., BOTOX; registered trademark; containing 100 units) is about 50 pg.

Therapeutic preparations of *botulinum* toxin are available from Allergan Inc. (U.S.A.), Ipsen Limited (U.K.) or Elan Pharmaceuticals (Ireland). These commercially available therapeutic preparations of *botulinum* toxin consist of a purified *botulinum* toxin complex (LL toxin) alone in a molecular structure bound with relevant non-toxic proteins. In recent years, type A NTX preparations (Merz Pharma, Xeomin (registered trademark), Germany) comprising no non-toxic proteins were sold in 2005, similar other preparations underwent clinical trials in the U.S.A. and development of next-generation preparations has actively been done.

The currently commercially available therapeutic preparations of type A *botulinum* toxin, i.e. BOTOX (registered trademark) from Allergan Inc. and Dysport (registered trademark) from Ipsen Limited, are consisted of a *botulinum* toxin complex (LL toxin) comprising as its component Haemagglutinin (HA) protein such as HA17, HA34, and HA70 (HA-positive).

On the other hand, a *botulinum* toxin isolated from patients suffering from infant botulism in 1990, though belonging to type A, is consisted of M toxin with no HA proteins (HA-negative). Type A *Clostridium botulinum* that produces M toxin with no HA protein has been first identified in Japan in 1986 from patients suffering from infant botulism (Non-patent reference 3). The clinically isolated strains include Kyoto-F, Chiba-H, Y-8036, 7I03-H, 7I05-H and KZ1828. When compared with the other types A to G of *botulinum* toxins, a *botulinum* toxin from *Clostridium botulinum* that causes infant botulism is a peculiar neurotoxin distinct from any types of these toxin molecules.

From the genetic point of view, a genetic mechanism of *Clostridium botulinum* as infant botulism pathogen is different from those of the other types of *botulinum* toxin. Most of the conventional *botulinum* toxins, typically type A *botulinum* toxin, has been seen as a *botulinum* toxin complex having Haemagglutinin (HA) protein as a component thereof. Genes coding for HA proteins such as HA17, HA34 and HA70 are included in neurotoxin genes of types A, B, C, D and G *Clostridium botulinum* but are completely absent in those of *Clostridium botulinum* as infant botulism pathogen. Also, genes of *Clostridium botulinum* as infant botulism pathogen include a regulator gene such as p47 (Non-patent reference 4). Besides, it was shown that a sequence of the NTNH protein of *botulinum* toxin produced by *Clostridium botulinum* as infant botulism pathogen is a miscellany, i.e. a mosaic, of non-toxic non-HA protein NTNH genes of type C and type A (Non-patent reference 5).

Furthermore, when *botulinum* toxin produced by *Clostridium botulinum* as infant botulism pathogen is compared with the conventional type A *botulinum* toxin comprising HA proteins, biochemical properties of the purified *botulinum* toxins are remarkably different from each other. The conventional type A *botulinum* toxin comprises the NTNH protein and at least three HA proteins (HA17, HA34 and HA70) whereas *botulinum* toxin produced by *Clostridium botulinum* as infant botulism pathogen comprises the NTNH protein alone but lacks the HA proteins (Non-patent reference 6). As for neurotoxin molecules per se, a molecular weight is distinct from each other in that a heavy chain of the conventional type A *botulinum* toxin is 93 kDa whereas *botulinum* toxin produced by *Clostridium botulinum* as infant botulism pathogen is 101 kDa. They also show different protease reactivity (Non-patent reference 7). The amino acid sequences of these two isotypes of the *botulinum* toxins are different by 89.9% as a whole and, in particular, there is great difference in the heavy chain regions, 109 among 847 amino acids (difference of 13%). On the other hand, it is reported that the light chains are different by 95.1% (Non-patent reference 8).

On the other hand, a problem has been presented that repetitive administration of *botulinum* toxin may diminish its efficacy. This phenomenon is thought to be due to production of antibodies against the toxin. It is pointed out that, as one of the causes, Haemagglutinin (HA) contained in therapeutic preparations has an adjuvant activity for antibody production (Non-patent reference 9).

For a highly purified *botulinum* toxin, it was formerly reported by Tse C K., et al. (Non-patent reference 10) and also in WO1996/11699 (Patent reference 1) as to a process for purification (p. 6, line 9 to p. 7, line 2) and pharmaceutical compositions (p. 11, Table 2).
Patent reference 1: WO1996/11699
Non-patent reference 1: Jankovic J. et al., Curr. Opin. Neurol., (7): p. 358-366, 1994
Non-patent reference 2: Ryuji Kaji et al., "Dystonia and *botulinum* therapy", Shindan-To-Chiryosha, 2005
Non-patent reference 3: Sakaguchi G. et al., Int. J. Food Microbiol., 11: p. 231-242, 1990
Non-patent reference 4: Kubota T. et al., FEMS Microbiology letters, 158: p. 215-221, 1998
Non-patent reference 5: Kubota T. et al., Biochem. Biophys. Res. Commun., 224(3): p. 843-848, 1996
Non-patent reference 6: Sakaguchi G. et al., Int. J. Food Microbiol. 11: p. 231-242, 1990
Non-patent reference 7: Kozaki S. et al., Microbiol. Immunol. 39(10): p. 767-774, 1995
Non-patent reference 8: Cordoba J. et al., System. Appl. Microbiol. 18: p. 13-22, 1995
Non-patent reference 9: Arimitsu H. et al., Infect. Immun., 71(3): p. 1599-1603, 2003
Non-patent reference 10: Tse C K. et al., Eur. J. Biochem., 122(3): p. 493-500, 1982

DISCLOSURE OF THE INVENTION

Technical Problem to be Solved by the Invention

*Botulinum* toxin is known as efficacious for the treatment of patients suffering from a disease with a muscle overactivity through relaxation of the muscles. However, where its action affects those sites other than desired portions, the action will be turned into toxicity. Accordingly, there is a social need for toxin preparations that may bring muscular tension into normal condition in case of contracture or systemic involuntary movement (restricted to cerebral palsy) and are highly safe, remain topically and may exhibit the efficacy soon. Besides, a problem has been presented that repetitive administration of *botulinum* toxin may diminish its efficacy. This phenomenon is thought to be due to production of antibodies against the toxin. It is pointed out that, as one of the causes, Haemagglutinin (HA) contained in therapeutic preparations has an adjuvant activity for antibody production. Therefore, a therapeutic medicament has been desired in which antibody production is not induced and repetitive administration does not diminish the efficacy. Although *botulinum* toxin preparations comprising LL toxin of *botulinum* toxin as a main active ingredient have been on market, development of preparations is desired that are superior to the conventional preparations in view of efficacy and adverse effects.

Means for Solving the Problems

Since mouse $LD_{50}$ has been used for potential unit of *botulinum* toxin preparations, a potential of *botulinum* toxin could only be compared by quantification of mouse $LD_{50}$. "Potential" refers to numerical expression of a desired efficacy of interest. Mouse $LD_{50}$, a measure for calculating an amount with which a half of mice subject to a test die within a fixed period of time, is a method for quantifying a potential unit from a concentration or a level of a toxin with which mice die as a consequence of relaxation and paralysis of the respiratory muscles and for judging "lethal activity" of a toxin within a fixed period of time. In this case, it is impossible to verify difference in property of *botulinum* toxins from viewpoint of time required for generating efficacy within a fixed period of time or adverse effects. As such, there was not an approach per se for estimating excellence of property in comparison with the commercially available *botulinum* toxin preparations.

Prior to the present invention, the present inventors initially have constructed a test system. Namely, the present inventors have developed a method for comparing rapid efficacy of potential of *botulinum* toxins by observing mouse $LD_{50}$ with lapse of time but not by estimating mouse $LD_{50}$ within a fixed period of time.

Besides, viewing that the desired efficacy of the *botulinum* toxin preparations currently on market is a relaxation activity to the muscles to be treated, it is desirable to evaluate an amount of *botulinum* toxins not by $LD_{50}$ but by quantification of a relaxation activity in such an extent that does not lead to lethality. Thus, efficacy of *botulinum* toxins is preferably referred to as an extent of a relaxation activity that is given by a certain amount of toxins to a certain muscle. The present inventors, by using an electromyograph, constructed a test system that allows for evaluation of efficacy to the muscles with time scale in clinic, i.e. a test system for quantifying a compound muscle action potential (CMAP), called a CMAP test system.

Using these systems, it has become possible to select more preferable molecular structure of *botulinum* toxins or bacterial strains from which said toxins are derived.

Furthermore, in order to find out a therapeutic medicament that is superior to the known *botulinum* toxin preparations, the present inventors focused on *botulinum* toxins produced by type A subspecies *Clostridium botulinum* as supposed to have the most highly lethal activity. This is a type A *botulinum* toxin comprising no HA proteins but M toxin that was isolated from patients suffering from infant botulism in 1990.

The present inventors, comparing the known LL toxin preparations and a highly purified *botulinum* neurotoxin (NTX) from *Clostridium botulinum* as infant botulism pathogen with each other by using the mouse $LD_{50}$ test with lapse of time and the CMAP test system as described above, have found out that the highly purified *botulinum* neurotoxin (NTX) is more excellent in rapid efficacy and is less diffusive than the LL toxin. As a consequence, the present inventors have found out that the highly purified *botulinum* neurotoxin (NTX) from *Clostridium botulinum* as infant botulism pathogen has a neuromuscular transmission blocking activity (a neuromuscular transmission blocking agent) and thus may most suitably be used as a medicament for treating a disease with a muscle overactivity. The highly purified *botulinum* neurotoxin (NTX) from *Clostridium botulinum* as infant botulism pathogen, as having rapid efficacy, is expected to exert efficacy more quickly at damaged portions. Also, it has advantage that it may be used as a safer preparation by avoiding spreading (diffusibility) of toxins to the muscles other than damaged portions. Besides, type A *Clostridium botulinum* isolated from patients suffering from infant botulism produce in part M toxin alone without HA proteins and thus has advantage that, for purification of neurotoxin, purification process for removing HA may be omitted due to complete absence of HA that enhances antibody production.

Effects of the Invention

The highly purified *botulinum* toxin (NTX) according to the present invention from HA-negative *Clostridium botulinum* isolated from infant botulism pathogen has a neuromuscular transmission blocking activity with more rapid efficacy than M toxin or LL toxin. A neuromuscular transmission blocking at the muscles away from those where *botulinum* toxin is administered, meaning adverse effects, is in the order of LL toxin>M toxin>NTX, suggesting that NTX is the least diffusive and has the lowest adverse effects.

As described above, NTX from infant botulism pathogen, when applied to the treatment of a disease with a muscle overactivity, has the features most favorable as a neuromuscular transmission blocking agent in that it exhibits "rapid efficacy" in the muscles of interest where tension needs to be relaxed whereas it does not relax tension in the muscles other than those of interest due to its "less diffusive" property. This is supposed to be due to an amino acid sequence peculiar to NTX from infant botulism pathogen and to its structure. The NTX preparation of the present invention has a great advantage that efficacy may be obtained in a shorter time after administration than the so-called LL toxin preparations such as BOTOX conventionally used for the treatment of a disease with a muscle overactivity and thus patients "may save several days before efficacy may be obtained". Furthermore, in case that the muscles with tension are large foot muscles which are used when human stands upright or walks, administration of a large amount, such as 300 units or more, of toxins is required. In such a case, relaxation of the muscles other than those of interest would possibly disturb the everyday life. Viewing that there is no appropriate antidotes to *botulinum* toxins, the feature of the NTX from infant botulism pathogen of being "less diffusive" is extremely advantageous in that it is "less risky in adverse effects".

Besides, the NTX preparation of the present invention, as comprising no HA thereby not likely to induce antibody production and not to diminish efficacy after repetitive administration, is useful as a medicament for treating a disease with a muscle overactivity such as strabismus, blepharospasm, hemifacial spasm, spasmodic torticollis, post-stroke spasticity, cerebral palsy, spasmodic dysphonia, headache such as migraine, chronic pain such as lumbago, the stiffness in the shoulders, paresis occurring at the onset of Parkinson disease or multiple sclerosis, myofascial pain syndrome, spasm of the masticatory muscles, chronic anal fissure, overactive bladder, bruxism, facial myokymia, tic, local dystonia, or wrinkle. In addition, since *botulinum* toxin is efficacious for alleviation of pains, the NTX preparation of the present invention will also be useful as a medicament for treating a variety of central nervous or peripheral nervous pains or postoperative pains.

BRIEF DESCRIPTION OF DRAWINGS

FIG. 1 illustrates a molecular structure of a *botulinum* toxin protein complex.

FIG. 2 is a graph showing time required for NTX toxin to exhibit efficacy with the $LD_{50}$ test with lapse of time using mice.

BEST MODE FOR CARRYING OUT THE INVENTION

Figure 3:
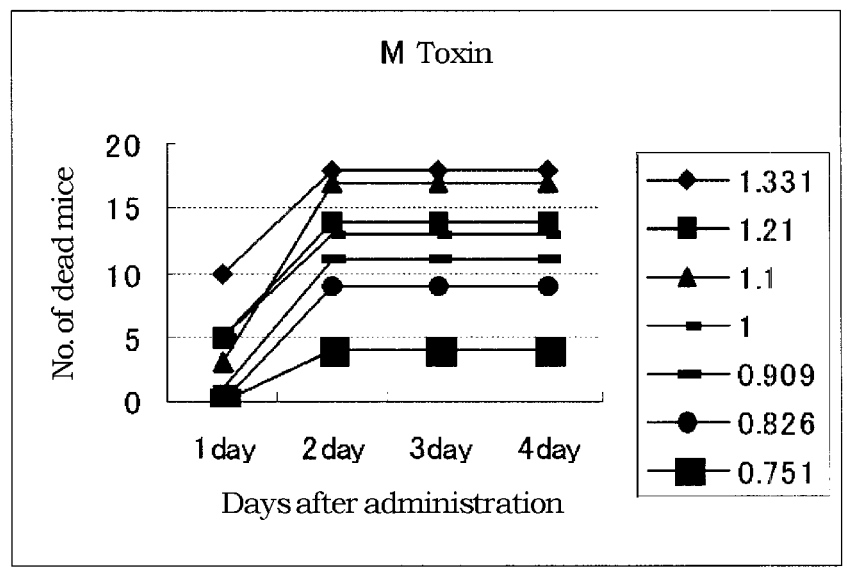
FIG. 3 is a graph showing time required for M toxin to exhibit efficacy with the $LD_{50}$ test with lapse of time using mice.

The therapeutic medicament of the highly purified type A *botulinum* toxin from infant botulism pathogen according to the present invention comprises as an active ingredient a highly purified type A *botulinum* toxin which is prepared by removing the non-toxic protein NTNH from M toxin obtained from HA-negative type A *Clostridium botulinum* isolated from infant botulism pathogen, i.e. NTX. Since NTX may exert efficacy more rapidly after administration as compared to LL toxin or M toxin, the therapeutic medicament of the present invention may be used as one with more rapid efficacy. Also, the highly purified type A *botulinum* toxin isolated as HA-negative infant botulism pathogen is less diffusive than the highly purified type A *botulinum* toxin obtained from HA-positive type A *botulinum* toxin and thus is an excellent a neuromuscular transmission blocking agent with a broader safety margin and may most suitably be used as a therapeutic medicament for decreasing local, muscle overactivity in a disease with a muscle overactivity.

Such a type of *botulinum* toxin as isolated from patients suffering from infant botulism, though being type A, consists of M toxin without HA proteins. Type A *Clostridium botulinum* that produce *botulinum* toxin without HA proteins are selected from Kyoto-F, Chiba-H, Y-8036, 7I03-H, 7I05-H and KZ1828.

The therapeutic medicament of the present invention is preferably a pharmaceutical composition comprising the highly purified type A *botulinum* toxin from infant botulism pathogen and a stabilizing agent for *botulinum* toxin.

A stabilizing agent for *botulinum* toxin may stabilize a *botulinum* toxin under conditions under which the composition as described above is stored and would not impair rapid efficacy of treating efficacy to a disease with a muscle overactivity. An example of a stabilizing agent for *botulinum* toxin includes a human serum albumin.

The preferable pharmaceutical composition of the present invention may be prepared by the step of mixing the highly purified type A *botulinum* toxin from infant botulism pathogen with a human serum albumin. Accordingly, the present invention also provides a process for preparing a pharmaceutical composition comprising a *botulinum* toxin which comprises the steps: (1) purifying a *botulinum* toxin and (2) mixing the *botulinum* toxin with a human serum albumin.

The highly purified type A *botulinum* toxin may be purified by a suitable combination of ion exchange chromatography, gel filtration chromatography, hydrophilic chromatography, and the like. Specifically, M toxin is concentrated from a culture supernatant of *Clostridium botulinum* by e.g. salting-out with ammonium sulfate or treatment with protamine. M toxin is then placed at pH 7 or more to be separated into a neurotoxin and non-toxic proteins. Then, the neurotoxin is crudely purified by e.g. cation exchange chromatography and the fractions with the toxic activity are collected and further purified by gel filtration chromatography. The toxic activity may be measured by e.g. intraperitoneal injection in mice, where the toxic activity is calculated from $LD_{50}$ after intraperitoneal administration in mice, and $LD_{50}$ in mice is defined as 1 unit.

After the purification step, any procedure may be taken insofar as comprising the step of mixing the *botulinum* toxin with a human serum albumin. For instance, the *botulinum* toxin and a stabilizing agent for *botulinum* toxin may be dissolved in a solvent and the solution may sterilely be filtered and filled into an ample, a vial, and the like to prepare the pharmaceutical composition of the present invention. Alternatively, the *botulinum* toxin may be dissolved in a solvent in which a stabilizing agent for *botulinum* toxin has previously been dissolved and the solution may sterilely be filtered and filled into an ample etc. A solvent may include distilled water for injection, physiological saline, 0.01M to 0.1M phosphate buffer, etc., which may optionally be mixed with ethanol, glycerol, etc.

Alternatively, the *botulinum* toxin and a stabilizing agent for *botulinum* toxin may be dissolved in a solvent, and the solution may sterilely be filtered and filled into a vial etc., followed by lyophilization to prepare the pharmaceutical composition of the present invention. Still alternatively, the *botulinum* toxin and a stabilizing agent for *botulinum* toxin may be mixed together and the mixture may then be sterilely filled into a vial etc. to prepare the pharmaceutical composition of the present invention.

Specifically, to the purified *botulinum* toxin may be added a stabilizing agent for *botulinum* toxin, preferably a human serum albumin, more preferably a human serum albumin for therapy proved for safety in human, at a final concentration of 0.1 to 5 mg/mL, preferably 0.5 to 2 mg/mL, and the mixture may be stored with cooling, freezing or by lyophilization.

The therapeutic medicament of the present invention, as occasion demands, may further be supplemented with additives such as sugars e.g. mannitol, glucose or lactose, a saline, sodium phosphate, and the like. The pharmaceutical composition of the present invention may usually be at pH of 3 to 8, preferably 4 to 7, more preferably 5 to 7.

The *botulinum* toxin contained in the therapeutic medicament of the present invention may be at such an amount as efficacious for use in the present invention. In case that a stabilizing agent for *botulinum* toxin is contained in the therapeutic medicament of the present invention, the agent may be at an amount sufficient for stabilizing the *botulinum* neurotoxin.

The therapeutic medicament of the present invention, as compared to the conventional known *botulinum* toxin preparations, has "rapid efficacy" of potential and a broader safety margin due to being "less diffusive" and thus may most suitably be used as a therapeutic medicament for decreasing local, muscle overactivity in a disease with a muscle overactivity. The objective diseases for which the therapy for decreasing local, muscle overactivity is aimed herein includes strabismus, blepharospasm, hemifacial spasm, spasmodic torticollis, post-stroke spasticity, cerebral palsy, spasmodic dysphonia, headache such as migraine, chronic pain such as lumbago, the stiffness in the shoulders, paresis occurring at the onset of Parkinson disease or multiple sclerosis, myofascial pain syndrome, spasm of the masticatory muscles, chronic anal fissure, overactive bladder, bruxism, facial myokymia, tic, local dystonia, or wrinkle. The myofascial pain syndrome, a disease with tension bands of solid stiffness in the muscles produced due to acute muscular damage or repetitive overload (overuse) of the muscles and with a strong pain, is known that muscular tension in hands and legs is exceedingly accelerated postapoplectically or in association with the onset of cerebral palsy, Parkinson disease or multiple sclerosis. It is also known that headache such as chronic migraine occurs due to abnormal muscle overactivity in the neck and the shoulders and that muscular tension may abnormally be accelerated due to fatigue in the muscles or sustained bad carriage to thereby ultimately induce chronic pains such as lumbago, pains at the neck or the back or the stiffness in the shoulders.

A disease with a muscle overactivity to be treated with the therapeutic medicament of the present invention is preferably a disease where rapid relaxation of a muscle overactivity is needed, i.e. a disease that needs to be treated with a therapeutic medicament having immediate efficacy. Such a disease with a muscle overactivity includes one where a medicament is administered by adjusting a dose until an effective dose is determined and systemic one where the treatment is done with cumulative efficacy. A systemic disease with a muscle overactivity includes systemic dystonia, systemic contracture, post-stroke spasticity, cerebral palsy, Parkinson disease and multiple sclerosis.

The therapeutic medicament of the present invention may be administered at an effective amount. When administered to human, its preferable route of administration is topical administration, more preferably, intramuscular administration. Timing and a dose of administration are not particularly limited and may vary depending upon severity of symptoms etc. A dose may vary depending upon severity of symptoms, age, sex, weight, site and route of administration but, for instance, 0.01 to 900 units, preferably 5 to 300 units are once administered intramuscularly for adults. One unit is defined herein as an amount of the toxin with which a half of mice die when administered intraperitoneally (1 $LD_{50}$). A total dose for patients is within a range of about 0.01 to 900 units.

After injection, therapy proceeds while it is confirmed in all patients that there is no extensive decrease in local tension in the muscles other than those of interest observed with no systemic or local adverse effects and that functional alleviation in the muscles to be treated is seen using an electromyograph.

The present invention also provides a method for the treatment by using the therapeutic medicament of the highly purified type A *botulinum* toxin from HA-negative type A *Clostridium botulinum* isolated as infant botulism pathogen for decreasing local, muscle overactivity in a disease with a muscle overactivity. The highly purified *botulinum* toxin, a disease with a muscle overactivity, a route of administration and a process for preparing the same are described hereinabove.

EXAMPLE

The present invention is explained in more detail by means of the following Examples but is not limited thereto.

Example 1

Purification of Type A *Botulinum* Neurotoxin

Using Chiba-H strain, type A *Clostridium botulinum* isolated from patients suffering from a disease with a muscle overactivity, *botulinum* type A, M toxin, was purified as described by Sakaguchi G., Biochemical aspects of botulism: Purification and oral toxicities of *Clostridium botulinum* progenitor toxins, 21-34, Lewis G E., 1981, Academic Press, New York.

The *botulinum* M toxin was dialyzed against 10 mM phosphate buffer (pH 7.5), adsorbed to DEAE Sepharose column equilibrated with the same buffer, and eluted with 0 to 0.3 M NaCl gradient of the same buffer to separate the neurotoxin from non-toxin proteins. The obtained highly purified neurotoxin (NTX) was concentrated with YM-10 membrane (Amicon) to 1 mg/mL, dialyzed against 50 mM phosphate buffer (pH 7.5) and stored at −80° C. till use.

Example 2

Figure 4:
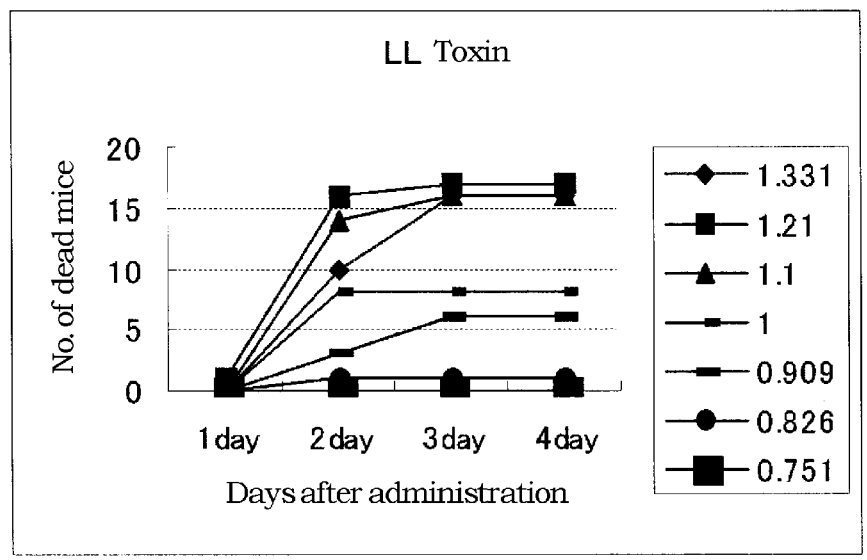
FIG. 4 is a graph showing time required for progenitor toxin to exhibit efficacy with the $LD_{50}$ test with lapse of time using mice.

Comparison of Time Required for Various Toxins to Exhibit Efficacy with $LD_{50}$ Test with Lapse of Time in Mice For the *botulinum* toxin, the type A, M toxin and NTX, as prepared in Example 1, were used. For LL toxin, BOTOX (registered trademark) manufactured by Allergan Inc. was used. Each of the toxins were diluted with a sample dilution Buffer to 2.662, B2.420, 2.200, 2.000, 1.818, 1.653, and 1.503 $LD_{50}$/mL (7 doses, interval×1.1 dilution). To each 20 mice per dilution group was intraperitoneally administered 0.5 mL of the toxin. For 4 days after administration, mice were observed for death everyday. The results are shown in FIGS. 2 to 4.

As a result, time for death was found to be in the order NTX>M toxin>LL toxin, demonstrating that NTX exhibited efficacy most immediately and could lead mice to death in less days.

Example 3

Comparison of CMAP for Various Neurotoxins

Figure 5:
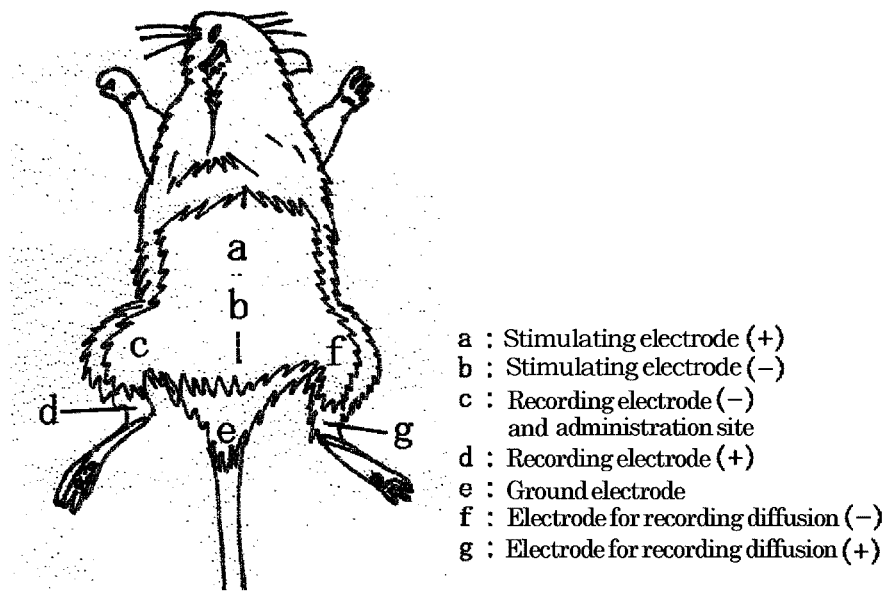
FIG. 5 shows sites where administered with *botulinum* toxins and sites where CMAP is measured.
Figure 6:
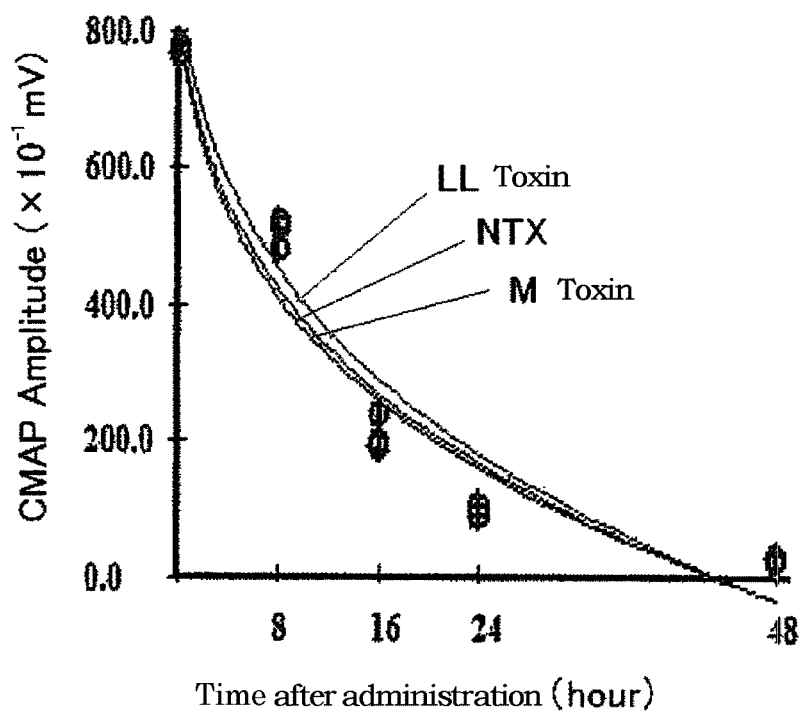
FIG. 6 is a graph showing the results of CMAP in the left hind leg muscle where various *botulinum* toxins were administered. The axis of abscissas depicts time after administration (hour) whereas the axis of ordinates CMAP amplitude (×10-1 mA).
Figure 7:
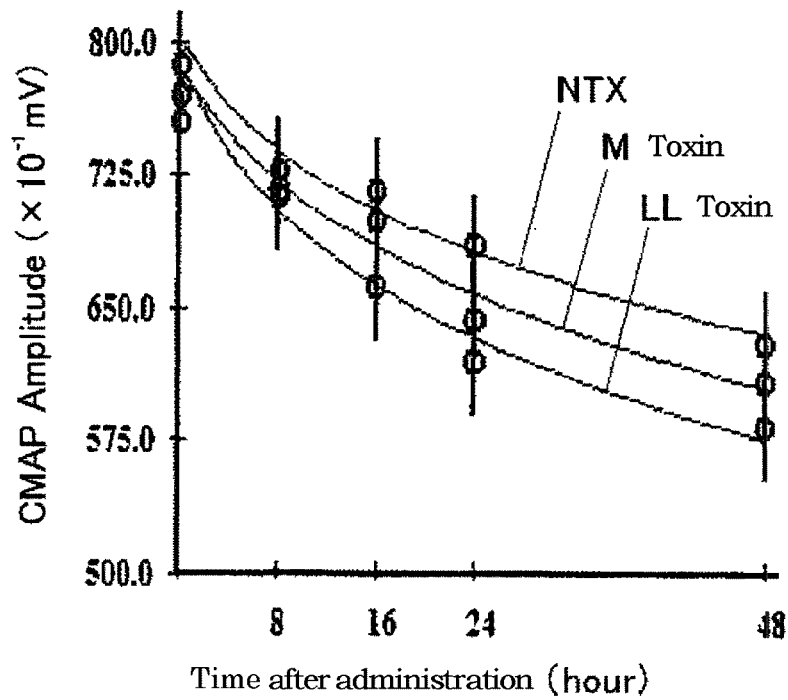
FIG. 7 is a graph showing the results of CMAP in the right hind leg muscle as opposite to the site where various *botulinum* toxins were administered. The axis of abscissas depicts time after administration (hour) whereas the axis of ordinates CMAP amplitude (×10-1 mA).

For the *botulinum* toxin, the type A, M toxin and NTX, as prepared in Example 1, were used. For LL toxin, BOTOX (registered trademark) manufactured by Allergan Inc. was used. For unit of each toxin, 1 unit was defined as 1 $LD_{50}$ when intraperitoneally administered to mice. Each toxin was prepared at mouse 3 $LD_{50}$/0.1 mL using sterile physiological saline containing 0.5% serum albumin. Each 0.1 mL of both toxins was administered to the gastrocnemius muscle of the left hind leg of each rat (SD) and a change in a compound muscle action potential (CMAP) of the hind legs was measured. For measurement of CMAP of the hind legs, the vicinity of the lumber of rat was nipped with a clip electrode to apply electric excitement and CMAP for each of the right and left hind legs was recorded with recording electrodes. FIG. 5 shows sites where the *botulinum* toxin was administered and sites where CMAP was measured. An electromyograph used was Nicolet Biking Quest series (Nicolet Biomedical). The results were numerically expressed with analytical software. FIGS. 6 and 7 show the CMAP results of each toxin of the left and right hind legs, respectively.

The CMAP results of the left hind leg where the *botulinum* toxin was administered revealed rapid efficacy of muscular relaxation in the order NTX>M toxin=LL toxin, demonstrating that NTX exhibited efficacy most immediately. Furthermore, according to the CMAP results of the right hind leg, opposite to the site where the *botulinum* toxin was administered, i.e. where the *botulinum* toxin was not administered, rapid efficacy of muscular relaxation and diffusibility were in the order LL toxin>M toxin>NTX, demonstrating that NTX is the least diffusive.

Example 4

Purification of NTX from HA-Positive Type A *Botulinum* Toxin

Using HA-positive type A *Clostridium botulinum*, 62A strain, the procedures of Example 1 were repeated to perform culture and purification of the toxins as described by Sakaguchi G., Biochemical aspects of botulism: Purification and oral toxicities of *Clostridium botulinum* progenitor toxins, 21-34, Lewis G E., 1981, Academic Press, New York. Furthermore, NTX was purified from M toxin and referred to as 62A NTX.

Example 5

Comparison of Therapeutic Window in Various Neurotoxins

For the *botulinum* toxin, the type A, NTX, as prepared in Example 1 and 62A NTX as prepared in Example 4 were used. For LL toxin, BOTOX (registered trademark) manufactured by Allergan Inc. was used. Each toxin was diluted to 136.0, 68.0, 34.0, 17.0, 4.0, 2.0, 1.0, and 0.50 $LD_{50}$/mL using sterile physiological saline containing 0.5% serum albumin.

Figure 8:
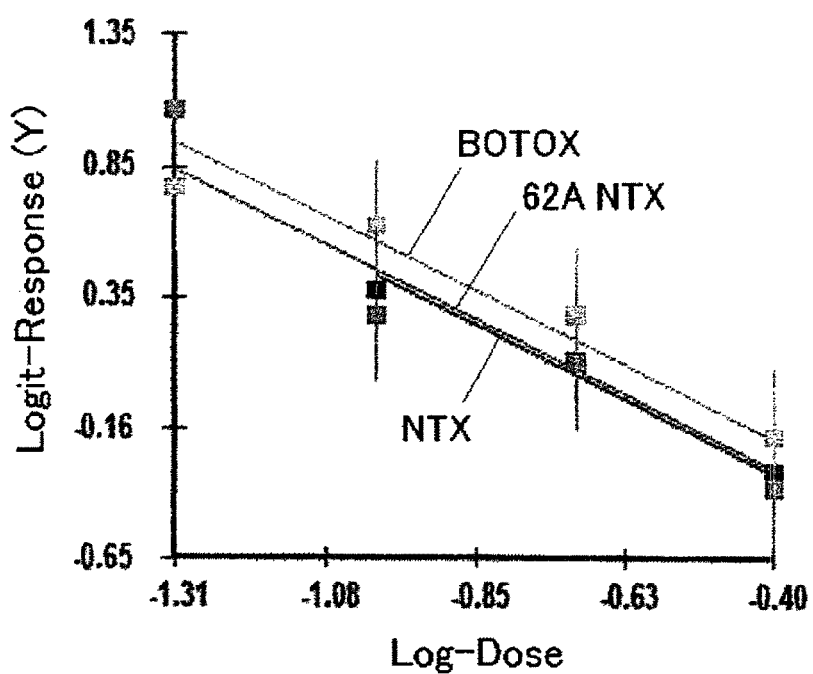
FIG. 8 is a graph showing linear regression of CMAP amplitude in the left hind leg at 1 day after the administration.
Figures 9, 10:
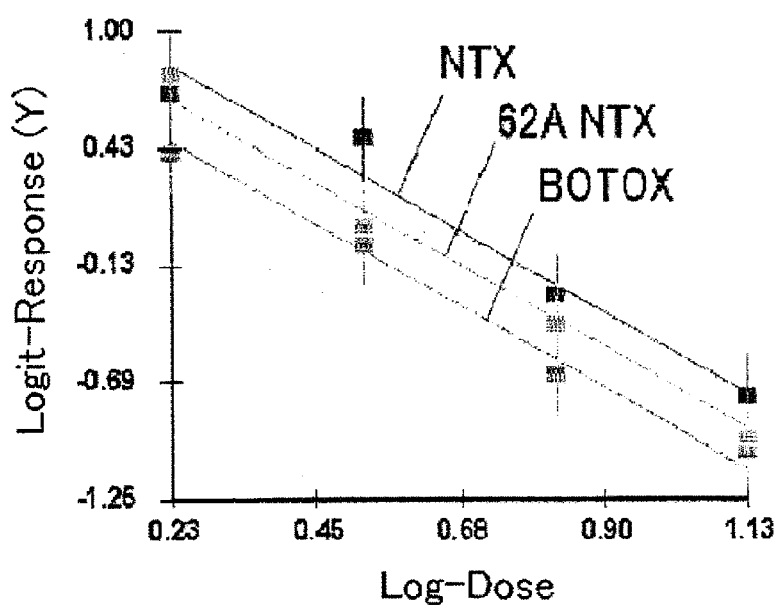
FIG. 9 is a graph showing linear regression of CMAP amplitude in the right hind leg at 4 days after the administration.
FIG. 10 shows comparison of the various toxins for $CMAP-ED_{50}$, $CMAP-SD_{50}$, and therapeutic window.

Each 0.1 mL of the diluted toxins was administered to the gastrocnemius muscle of the left hind leg of each rat (SD) and CMAP was measured for the left hind leg at 1 day after administration and for the right hind leg at 4 days after administration. CMAP-ED$_{50}$ was defined as a toxic activity decreased by 50% at 1 day after administration in the left hind leg. CMAP-SD$_{50}$ was defined as a toxic activity decreased by 50% at 4 days after administration in the right hind leg. Also, therapeutic window was defined as CMAP-SD$_{50}$ divided by CMAP-ED$_{50}$. FIG. 8 shows linear regression of CMAP amplitude in the left hind leg at 1 day after the administration. FIG. 9 shows linear regression of CMAP amplitude in the right hind leg at 4 days after the administration. FIG. 10 shows comparison of the various toxins for CMAP-ED$_{50}$, CMAP-SD$_{50}$, and therapeutic window.

As shown in FIG. 10, CMAP-ED$_{50}$ was almost the same among each of the toxins whereas CMAP-SD$_{50}$ revealed that NTX is the least diffusive as requiring the highest toxic activity for affecting the site where the toxin was not administered with a ratio of NTX to 62A NTX being 1.8 and a ratio of NTX to BOTOX being 1.45. Comparing each toxin for Therapeutic window, NTX has about twice broader value and thus can be said to be the most suited for the therapy.

INDUSTRIAL APPLICABILITY

The therapeutic medicament of the highly purified type A *botulinum* toxin from infant botulism pathogen according to the present invention comprises as an active ingredient a highly purified type A *botulinum* toxin which is prepared by removing the non-toxic protein NTNH from M toxin obtained from HA-negative type A *Clostridium botulinum* isolated from infant botulism pathogen, i.e. NTX. Since NTX may exert efficacy more rapidly after administration as compared to LL toxin or M toxin, the therapeutic medicament of the present invention may be used as one with more rapid efficacy. Also, the highly purified type A *botulinum* toxin isolated as HA-negative infant botulism pathogen is less diffusive than the highly purified type A *botulinum* toxin obtained from HA-positive type A *botulinum* toxin and thus has a broader safety margin and may most suitably be used as a therapeutic medicament for decreasing local, muscle overactivity in a disease with a muscle overactivity.

The invention claimed is:

1. A neuromuscular transmission blocking agent, comprising, as an active ingredient, a highly purified *botulinum* toxin type A S toxin (NTX), an active center protein, that is from hemagglutinin-non-producing *Clostridium botulinum* type A isolated as infant botulism pathogen, that is not in a complex with a non-toxic protein (NTNH), and that does not comprise hemagglutin (HA) proteins, wherein said *botulinum* toxin type A S toxin (i) has a molecular weight of 150 kDa and (ii) has a broader therapeutic window, a broader safety margin, and exhibits a more rapid efficacy and a less diffusive property than *botulinum* toxins LL, L and M.

2. The neuromuscular transmission blocking agent of claim 1, wherein said highly purified *botulinum* toxin type A is produced by any HA-negative strain of Kyoto-F, Chiba-H, Y-8036, 7I03-H, 7I05-H, or KZ1828 derived from infant botulism pathogen.

3. The neuromuscular transmission blocking agent of claim 1, which further comprises a stabilizing agent for *botulinum* toxin.

4. The neuromuscular transmission blocking agent of claim 3, wherein said stabilizing agent is a human serum albumin.

5. A medicament for treating a disease with a muscle overactivity, comprising, as an active ingredient, a highly purified *botulinum* toxin type A S toxin (NTX), an active center protein, that is from HA-non-producing *Clostridium botulinum* type A isolated as infant botulism pathogen, that is not in a complex with a non-toxic protein (NTNH), and that does not comprise HA proteins, wherein said *botulinum* toxin type A S toxin (i) has a molecular weight of 150 kDa and (ii) has a broader therapeutic window, a broader safety margin, and exhibits a more rapid efficacy and a less diffusive property than *botulinum* toxins LL, L and M.

6. The medicament of claim 5, wherein said highly purified *botulinum* toxin type A is produced by any HA-negative strain of Kyoto-F, Chiba-H, Y-8036, 7I03-H, 7I05-H, or KZ1828 derived from infant botulism pathogen.

7. The medicament of claim 5, wherein said disease with a muscle overactivity is a disease induced by local overactivity, said disease being selected from strabismus, blepharospasm, hemifacial spasm, spasmodic torticollis, post-stroke spasticity, cerebral palsy, spasmodic dysphonia, headache, chronic pain, the stiffness in the shoulders, paresis occurring at the onset of Parkinson disease or multiple sclerosis, myofascial pain syndrome, spasm of the masticatory muscles, chronic anal fissure, overactive bladder, bruxism, facial myokymia, tic, local dystonia, or wrinkle.

8. The medicament of claim 5, which further comprises a stabilizing agent for *botulinum* toxin.

9. The medicament of claim 8, wherein said stabilizing agent is a human serum albumin.

10. The medicament of claim 7, wherein the headache is a migraine headache.

11. The medicament of claim 7, wherein the chronic pain is lumbago.

* * * * *